United States Patent
Keinan et al.

(10) Patent No.: US 10,507,139 B2
(45) Date of Patent: Dec. 17, 2019

(54) WOUND DRESSING APPARATUS AND METHOD OF USE THEREOF

(71) Applicant: FIRST CARE PRODUCTS LTD., Roah HaAin (IL)

(72) Inventors: Emanuel Keinan, Tel Aviv (IL); Roee Madai, Givat Ada (IL)

(73) Assignee: FIRST CARE PRODUCTS LTD., Rosh Haain (IL)

( * ) Notice: Subject to any disclaimer, the term of this patent is extended or adjusted under 35 U.S.C. 154(b) by 482 days.

(21) Appl. No.: 15/314,270

(22) PCT Filed: May 28, 2015

(86) PCT No.: PCT/IL2015/050558
§ 371 (c)(1),
(2) Date: Nov. 28, 2016

(87) PCT Pub. No.: WO2015/181828
PCT Pub. Date: Dec. 3, 2015

(65) Prior Publication Data
US 2017/0196734 A1    Jul. 13, 2017

Related U.S. Application Data

(60) Provisional application No. 62/004,237, filed on May 29, 2014.

(51) Int. Cl.
*A61F 13/02* (2006.01)
*A61F 13/00* (2006.01)

(52) U.S. Cl.
CPC .. *A61F 13/00029* (2013.01); *A61F 13/00021* (2013.01); *A61F 13/00085* (2013.01); *A61F 13/0203* (2013.01); *A61F 13/0273* (2013.01); *A61F 2013/00102* (2013.01); *A61F 2013/00106* (2013.01); *A61F 2013/00119* (2013.01)

(58) Field of Classification Search
CPC ............ A61F 2013/00089–2013/00357; A61F 13/00029
See application file for complete search history.

(56) References Cited

U.S. PATENT DOCUMENTS

| | | |
|---|---|---|
| 34,112 A | 1/1862 | Lambert |
| 721,162 A | 2/1903 | Denain |
| 2,113,534 A | 4/1938 | Brown |

(Continued)

FOREIGN PATENT DOCUMENTS

| | | |
|---|---|---|
| DE | 29611673 U1 | 10/1996 |
| GB | 836258 | 6/1960 |

OTHER PUBLICATIONS

"Definition of remove," Merriam-Webster dictionary, printed Apr. 29, 2019.*

(Continued)

*Primary Examiner* — Susan S Su
(74) *Attorney, Agent, or Firm* — The Roy Gross Law Firm, LLC; Roy Gross

(57) ABSTRACT

The present disclosure provides, inter-alia, an apparatus for wound-dressing. In particular, embodiments of the disclosure provide a wound-dressing apparatus comprising a wrapping element and a pad element, wherein the pad element is foldable and comprises at least one removable portion.

19 Claims, 8 Drawing Sheets

(56) References Cited

U.S. PATENT DOCUMENTS

| | | | | |
|---|---|---|---|---|
| 2,292,995 | A | * | 8/1942 | Greenwoll ............ A61F 15/001 206/441 |
| 2,337,011 | A | * | 12/1943 | Young ................... A61F 15/006 602/42 |
| 2,453,705 | A | * | 11/1948 | Gallagher ......... A61F 13/00021 206/440 |
| 2,480,430 | A | | 8/1949 | Walters |
| 2,560,712 | A | * | 7/1951 | Bell .................... A61F 13/0273 602/53 |
| 2,572,641 | A | * | 10/1951 | Manley ............... A61F 13/0203 428/486 |
| 2,646,034 | A | | 7/1953 | Chapados |
| 3,005,454 | A | | 10/1961 | Bird |
| 3,050,064 | A | | 8/1962 | Moore |
| 3,125,093 | A | * | 3/1964 | Hutchins ............. A61F 13/0273 128/DIG. 15 |
| 3,421,502 | A | * | 1/1969 | St. Clair ........... A61F 13/00072 206/440 |
| 3,536,068 | A | | 10/1970 | Stubbs |
| 3,625,209 | A | * | 12/1971 | Clark ................ A61F 13/00021 602/44 |
| 3,653,382 | A | * | 4/1972 | Easley ................. A47G 9/0207 604/370 |
| 3,867,935 | A | * | 2/1975 | Eisdorfer .......... A61F 13/00034 604/385.201 |
| 3,920,010 | A | * | 11/1975 | Chesky ............. A61F 13/00029 602/53 |
| 4,048,991 | A | | 9/1977 | Marx |
| 4,149,540 | A | | 4/1979 | Hasslinger |
| 4,214,581 | A | * | 7/1980 | Bergman .......... A61F 13/00021 602/58 |
| 4,243,028 | A | | 1/1981 | Puyana |
| 4,345,591 | A | | 8/1982 | Hedgren |
| 4,655,209 | A | | 4/1987 | Scott |
| 4,748,978 | A | * | 6/1988 | Kamp .................... A61L 15/18 424/445 |
| 4,802,667 | A | | 2/1989 | Altner |
| 4,819,622 | A | * | 4/1989 | Taylor .................... A61F 5/055 128/DIG. 23 |
| 4,983,173 | A | * | 1/1991 | Patience ........... A61F 13/00008 604/384 |
| 4,984,570 | A | * | 1/1991 | Langen ............. A61F 13/00008 602/44 |
| 5,234,459 | A | | 8/1993 | Lee |
| 5,628,723 | A | | 5/1997 | Grau |
| 6,162,959 | A | * | 12/2000 | O'Connor ......... A61F 13/15658 602/41 |
| 8,163,973 | B2 | | 4/2012 | Johnson |
| 2005/0256438 | A1 | * | 11/2005 | Lombardozzi ...... A61F 13/0203 602/53 |
| 2007/0066924 | A1 | * | 3/2007 | Hopman .......... A61F 13/00034 602/48 |
| 2010/0137774 | A1 | * | 6/2010 | Hofstetter ......... A61F 13/00029 602/44 |
| 2010/0158989 | A1 | * | 6/2010 | Mentkow .......... A61F 13/00063 424/447 |
| 2010/0262090 | A1 | * | 10/2010 | Riesinger .......... A61F 13/00017 604/304 |
| 2011/0288463 | A1 | * | 11/2011 | Girasa .................. A61F 15/002 602/57 |
| 2011/0288509 | A1 | | 11/2011 | Bar Natan et al. |
| 2012/0065566 | A1 | * | 3/2012 | Bar-Natan ........ A61F 13/00085 602/53 |
| 2013/0060217 | A1 | * | 3/2013 | Mouton ................ A61F 13/069 604/372 |

OTHER PUBLICATIONS

Written Opinion for PCT/IL2015/050558 Completed Nov. 19, 2015; dated Nov. 26, 2015 5 pages.

International Search Report for PCT/IL2015/050558 Completed Nov. 19, 2015; dated Nov. 26, 2015 3 pages.

* cited by examiner

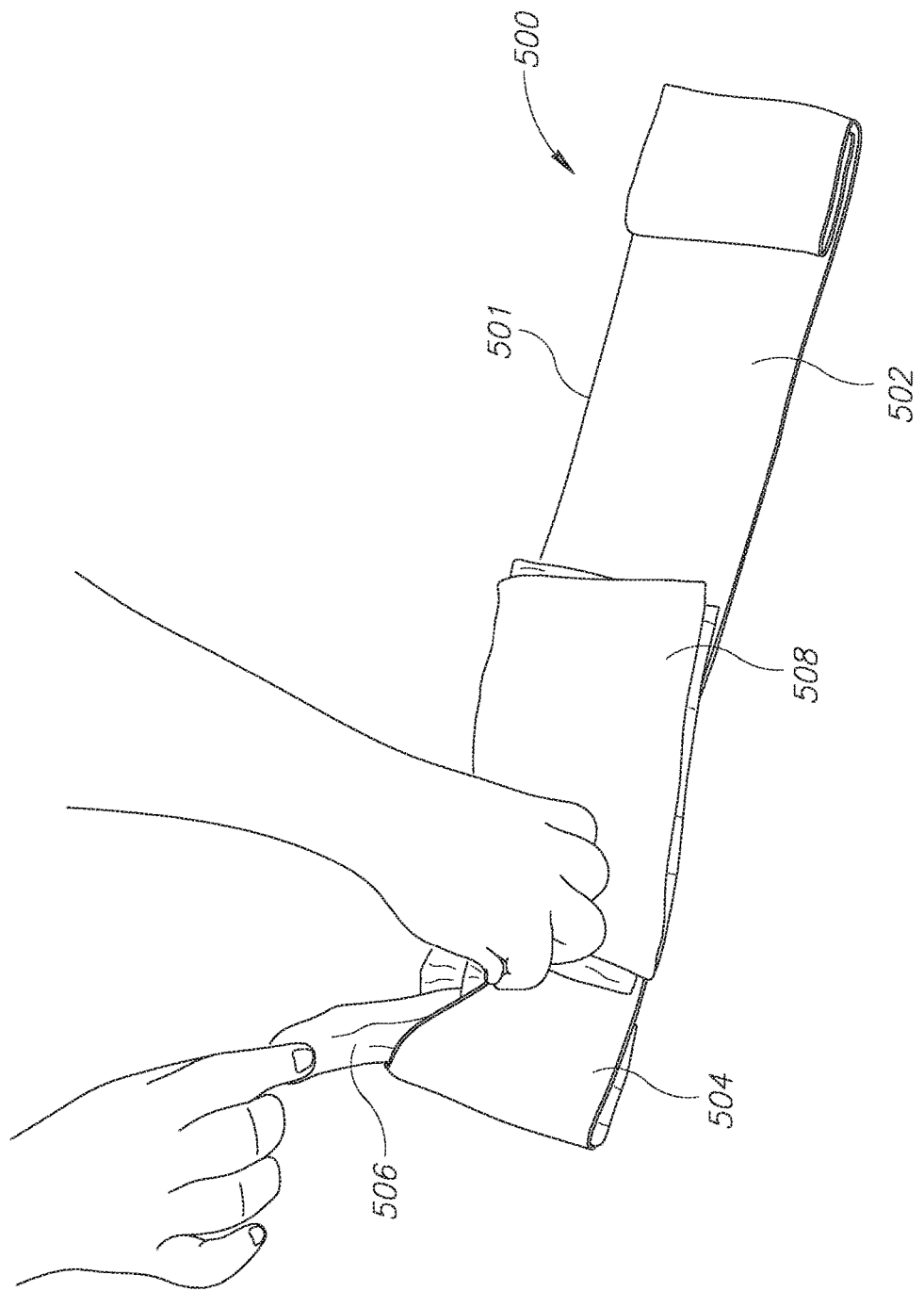

WOUND DRESSING APPARATUS AND METHOD OF USE THEREOF

This application is a 35 U.S.C. § 371 national phase application of PCT/IL2015/050558, filed May 28, 2015, which claims priority to U.S. 62/004,237 filed on May 29, 2014. Both applications are incorporated herein by reference as if fully set forth.

TECHNICAL FIELD

The present disclosure relates generally to bandages and methods of using same.

BACKGROUND

Wounds, which lead to a severe blood loss, are a main cause of death in battlegrounds and field conditions. Therefore, means for a quick and efficient bleeding stoppage is an essential first-aid treatment of such wounds.

Although there are many devices and methods useful in stopping bleeding, one of the most commonly used devices are bandages. Various types of bandages are known in the literature and markets. The following publications are believed to represent the current state of the art: U.S. Pat. Nos. 34,112; 721,162; 2,113,534; 2,480,430; 2,646,034; 3,005,454; 3,050,064; 3,536,068; 4,048,991; 4,149,540; 4,243,028; 4,345,591; 4,802,667; 5,234,459; 5,628,723 and 8,163,973.

Although various shapes and sizes of bandages exist in the market, these bandages may not fit a specific injury, especially battlefield injuries such as bullet wounds. Attempting to modify a standard bandage to fit a specific wound may require time that may lead to additional blood loss in the critical minutes following injury. There is, therefore, a need in the art for a bandage, which may be easily modified to fit complex wounds, such as bullet wounds having both an entry and an exit wound, amputations, large area wounds and multiple injuries.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods that are meant to be exemplary and illustrative, not limiting in scope.

The present disclosure provides, according to some embodiments, wound-dressing apparatus, which enable treatment of complex wounds, such as, but not limited to, wounds having an entry and an exit wound, amputations, large area wounds and multiple injuries. According to some embodiments, the disclosed wound-dressing apparatus comprises a foldable pad element which is configured to be in a folded position when packed and un-folded prior to use. According to some embodiments, unfolding of the foldable pad element provides a large pad, which can be used in dressing large wounds. According to some embodiments, at least part of the foldable pad is configured to be torn upon pulling. According to some embodiments, the torn part of the pad element may be used to clean the wound prior to dressing with the disclosed apparatus. According to other embodiments, the torn part of the pad element may be used to provide further packing and absorbing material while dressing a wound using the disclosed apparatus. According to yet other embodiments, the torn part of the pad element may be secured to a desired location on the wrapping element of the disclosed apparatus. According to some embodiments, securing part of the pad element to dress an exit wound, while a second part of the pad element dresses an entry wound, enables one to effectively dress a complex wound, such as, but not limited to, a bullet wound, using the same apparatus. Advantageously, the pad element having a detachable part enables one to quickly dress a wound having two foci, such as, but not limited to, bullet wounds having an entry and an exit wound.

According to one aspect, the present disclosure provides a wound-dressing apparatus, the apparatus comprising an elongated wrapping element and a foldable pad element; wherein said pad element comprises a first portion attached to a second portion, each portion comprising at least one absorbent layer;
wherein at least part of said first portion is attached to a first surface of said wrapping element such that said at least one absorbent layer faces away from said first surface;
wherein said second portion is configured to have an open position and a closed position, such that when said second portion is in the open position, said at least one absorbent layer faces away from the first surface of said wrapping element;
and wherein said second portion is configured to be removed from said first portion.

According to some embodiments, the elongated wrapping element has a first and second end; wherein one of said first or second ends of said elongated wrapping element comprises a compartment having at least one opening; wherein said compartment contains wound-dressing material; and wherein said wound-dressing material is configured to be extracted from said compartment upon pulling. According to some embodiments, the wound-dressing material is configured to be extracted from said compartment following a single pulling movement. According to some embodiments, the wound-dressing material is selected from the group consisting of: gauze, a bandage and a combination thereof. Each possibility represents a separate embodiment of the present invention. According to some embodiments, the wrapping element is elastic. According to some embodiments, the first portion of the pad element is juxtaposed with the compartment in the wrapping element.

According to some embodiments, the wound-dressing material extracted from the compartment in the wrapping element may be used to provide cleaning and/or further packing of the wound that is dressed using the disclosed apparatus. Each possibility represents a separate embodiment of the present invention.

According to some embodiments, at least part of the first portion of the pad element is integrally formed with the first surface of the wrapping element. According to some embodiments, the first surface of the wrapping element is a surface, which is configured to face the body of a subject in need thereof. As used herein, the term "a subject in need thereof" refers to a subject having a wound, such as, but not limited to, a wound having an entry and exit wound, amputations, large area wounds and multiple injuries. According to some embodiments, the pad element comprises an inner layer attached to at least one absorbent layer. According to some embodiments, the inner layer is composed of a non-permeable material, such as, but not limited to, plastic. According to some embodiments, the inner layer of the first portion of the pad element is attached to the first surface of the wrapping element. According to some embodiments, the inner layer of the first portion of the pad element is integrally formed with the first surface of the wrapping element. According to some embodiments, at least part of said first portion is integrally formed with said first surface of the wrapping element.

According to some embodiments, the second portion of the pad element extends beyond the first portion and the first surface of the wrapping element when it is in the open position. Without wishing to be bound by any mechanism, when the second portion is in the open position it forms a large absorbent area together with the first portion, thus enabling dressing of large wounds using the disclosed apparatus.

According to some embodiments, the second portion is configured to be at least partly folded over the first portion when in the closed position. According to some embodiments, the at least one absorbent layer of the second portion is configured to face the at least one absorbent layer of the first portion when in the closed position.

According to some embodiments, the second portion is reversibly sewn to the first portion. According to some embodiments, at least part of the second portion is reversibly attached to at least part of the first portion. According to some embodiments, the second portion is configured to be removed from the first portion upon pulling of said second portion. According to some embodiments, the second portion is configured to be removed from said first portion following a single pulling movement of the second portion. According to some embodiments, the second portion comprises a pull-tab or any other suitable handle or element configured to facilitate grasping by a user, thereby easing removal and/or detachment of said second portion from said first portion.

According to some embodiments, the second portion of the pad element is attached to the first portion of the pad element via at least one layer; wherein the at least one layer is attached to the first and second portions on opposing ends of the layer. According to some embodiments, the at least one layer is at least one absorbent layer. According to some embodiments, at least part of the second portion of the pad element is configured to be positioned below the at least one connecting layer when in the open position.

According to some embodiments, the second portion is configured to be attached to the first surface of said wrapping element following removal from the first portion. According to some embodiments, the first surface of said wrapping element comprises fixation means configured to attach said second portion to said first surface. According to some embodiments, the fixation means are selected from the group consisting of: adhesive strips, hook and loop fasteners and a combination thereof. Each possibility represents a separate embodiment of the present invention. Without wishing to be bound by any theory or mechanism, when the disclosed apparatus is used to dress complex wounds, such as, but not limited to, a wound having an entry and an exit wound, the second portion of the pad element can be torn and affixed to the first surface of the wrapping element. Placing the first portion near the entry wound, affixing the second portion at the position of the exit wound and wrapping the wrapping element around both may enable efficient and quick dressing of the complex wound.

According to some embodiments, the at least one absorbent layer is formed of a non-woven material.

According to some embodiments, the disclosed apparatus further comprises a third portion attached to said first portion, wherein said third portion is configured to have an open position and a closed position, such that when said third portion is in the open position, at least one absorbent layer of said third portion faces away from the first surface of said wrapping element; and wherein said third portion is configured to be removed from said first portion.

According to some embodiments, the present disclosure provides the disclosed apparatus for use in treating a complex wound. According to some embodiments, a complex wound may include wounds having at least an entry wound and an exit wound, amputations, large area wounds and multiple injuries as well as any other suitable complex wound and/or combinations thereof. According to some embodiments, the complex wound is a gunshot wound.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIG. 5 schematically illustrates a wound-dressing apparatus according to an embodiment of the present disclosure in which wound-dressing material is being extracted from a compartment in the wrapping element of the apparatus.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to one aspect, the present disclosure provides a wound-dressing apparatus, the apparatus comprising an elongated wrapping element and a foldable pad element; wherein said pad element comprises a first portion attached to a second portion, each portion comprising at least one absorbent layer;

wherein at least part of said first portion is attached to a first surface of said wrapping element such that said at least one absorbent layer faces away from said first surface;

wherein said second portion is configured to have an open position and a closed position, such that when said second portion is in the open position, said at least one absorbent layer faces away from the first surface of said wrapping element;

and wherein said second portion is configured to be removed from said first portion.

Figure 1:
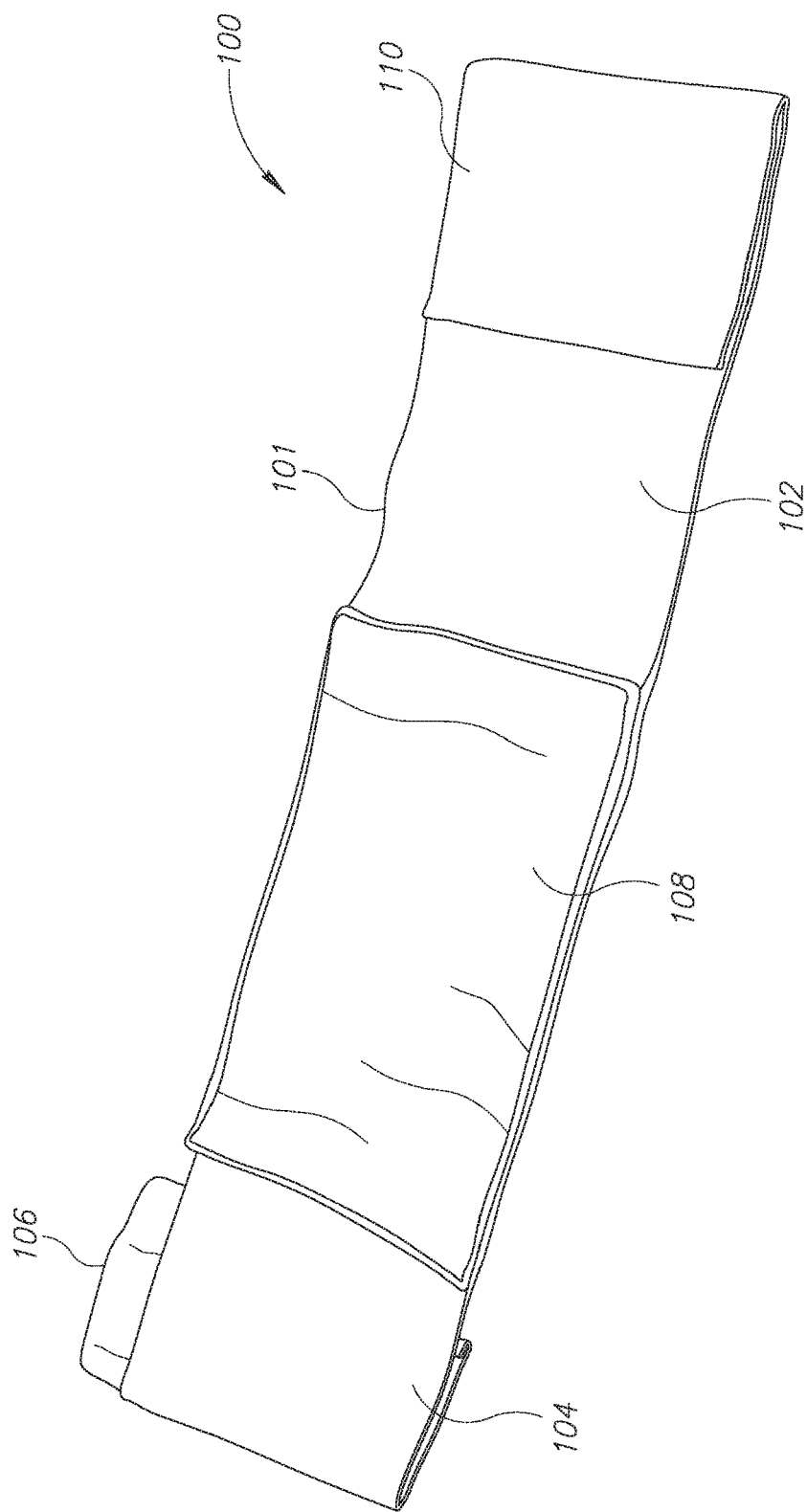
FIG. 1 schematically illustrates a wound-dressing apparatus according to an embodiment of the present disclosure.

Reference is now made to FIG. 1, depicting wound-dressing apparatus (100) according to an embodiment of the present disclosure. Wound-dressing apparatus (100) comprises wrapping element (101) and foldable pad element (108) at least partly attached to first surface (102) of wrapping element (101). As depicted in FIG. 1, foldable pad element (108) is shown in a folded position in which the second portion of the pad element is folded onto the first portion of the pad element, such that the absorbent layers of both portions are touching and not depicted in FIG. 1. According to some embodiments, elongated wrapping element (101) is elastic. According to some embodiments, elongated wrapping element (101) is configured to hold at least one part of folded pad element (108) securely over a wound and/or to stop bleeding from the wound. Each possibility represents a separate embodiment of the present invention.

Wrapping element (101) has receptacle (104) at a first end. Receptacle (104) comprises wound-dressing material (106) which may be extracted through an opening in receptacle (104). According to some embodiments, wound-dressing material (106) may be used for packing a wound treated by the disclosed apparatus. As used herein, the term "packing" may refer to applying and/or inserting a wound-dressing material, such as, but not limited to, gauze into the wound in order to cause internal pressure on the source of bleeding, thereby stopping, inhibiting and/or reducing bleeding. According to some embodiments, the wound-dressing material is sterile. According to some embodiments, a packing material refers to a wound-dressing material, such as, but not limited to, gauze. The second end (110) of wrapping element (101) is depicted rolled and may be extended and wrapped to fasten the apparatus to a subject in need thereof.

Figure 2A:
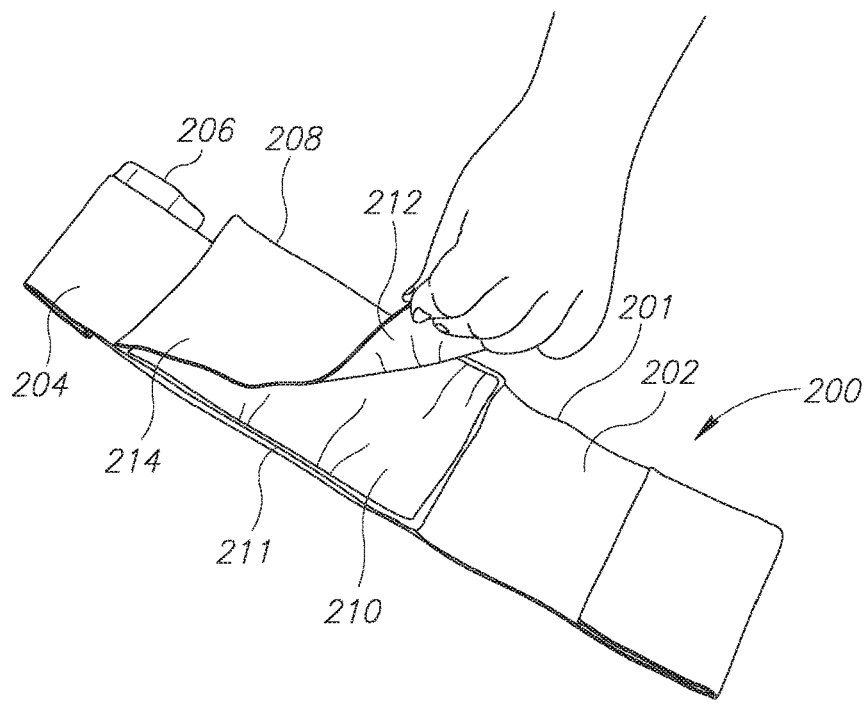
FIG. 2A and FIG. 2B schematically illustrates a wound-dressing apparatus according to an embodiment of the present disclosure, wherein the pad element is unfolded to the open position.
Figure 2B:
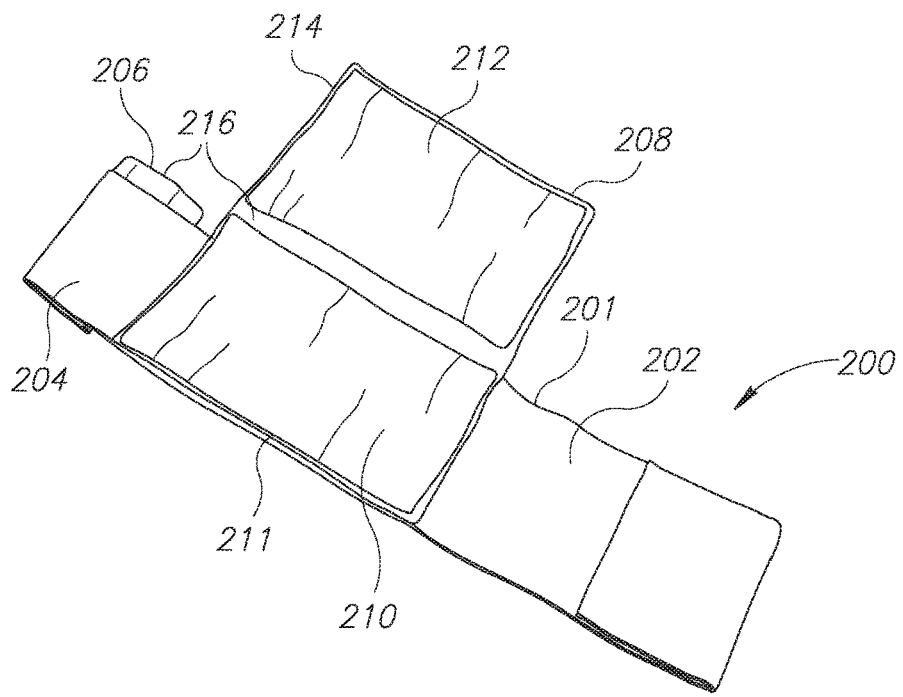

Reference is now made to FIGS. 2A and 2B, depicting wound-dressing apparatus (200) according to an embodiment of the present disclosure, in which foldable pad element (208) is being transferred from the closed to the open position. As depicted, at least part of first portion (211) of foldable pad element (208) is attached to first surface (202) of wrapping element (201). FIG. 2A shows second portion (214) of foldable pad element (208) being elevated from the closed to open position, thus exposing absorbent layers (210) and (212) of first and second portions (211 and 214), respectively. FIG. 2B depicts foldable pad element (208) in the open position, in which absorbent layers (210) and (212) of first and second portions (211 and 214), respectively, are exposed. According to some embodiments, unfolding the foldable pad element to the open position results in a larger absorbent layer, enabling to treat a large wound using the disclosed apparatus. First portion (211) of pad element (208) is attached to second portion (214) through attachment (216). According to some embodiments, attachment (216) may be any form of attachment enabling quick removal of second portion (214) from first portion (211). According to some embodiments, attachment (216) is thread, such that first portion (211) and second portion (214) are sewn together. According to some embodiments, attachment (216) is configured to enable removal of second portion (214) from first portion (211) by pulling second portion (214). Optionally, second portion (214) includes a handle such as a pull-tab (not shown), allowing grasping by a user, thereby easing the removal of second portion (214) from first portion (211).

According to some embodiments, at least part of first portion (211) of pad element (208) is attached to first surface (202) of wrapping element (201). According to some embodiments, first portion (211) comprises at least one absorbent layer (210) and further comprises at least one inner layer through which it is attached to wrapping element (201). According to some embodiments, the inner layer of first portion (211) is situated between first surface (202) and absorbent layer (210). According to some embodiments, at least part of first portion (211) is integrally formed with wrapping element (201). According to some embodiments, the inner layer of first portion (211) is integrally formed with wrapping element (201). According to some embodiments, attachment (216) attaches the inner layer of first portion (211) with the inner layer of second portion (214). According to some embodiments, the inner layers of first portion (211) and second portion (214) are integrally formed with wrapping element (201). According to some embodiments, the at least one absorbent layer is attached to and/or integrally formed with the inner layer. Each possibility represents a separate embodiment of the present invention.

Wound-dressing apparatus (200) further comprises compartment (204) which contains wound-dressing material (206) that may be extracted through an opening in compartment (204).

Figure 3A:
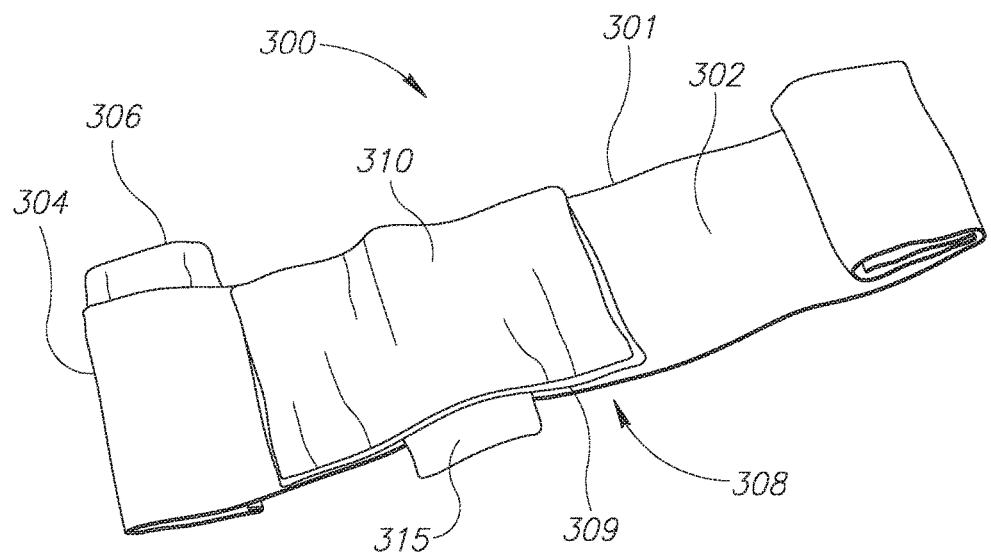
FIG. 3A, FIG. 3B and FIG. 3C schematically illustrate a wound-dressing apparatus according to an embodiment of the present disclosure.
Figure 3B:
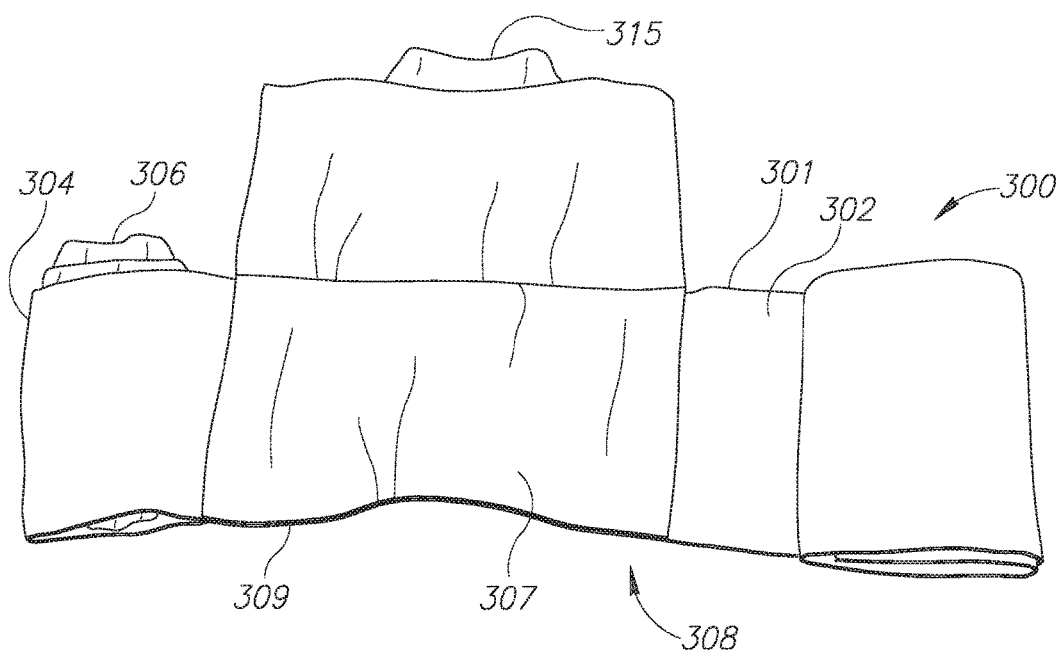
Figure 3C:
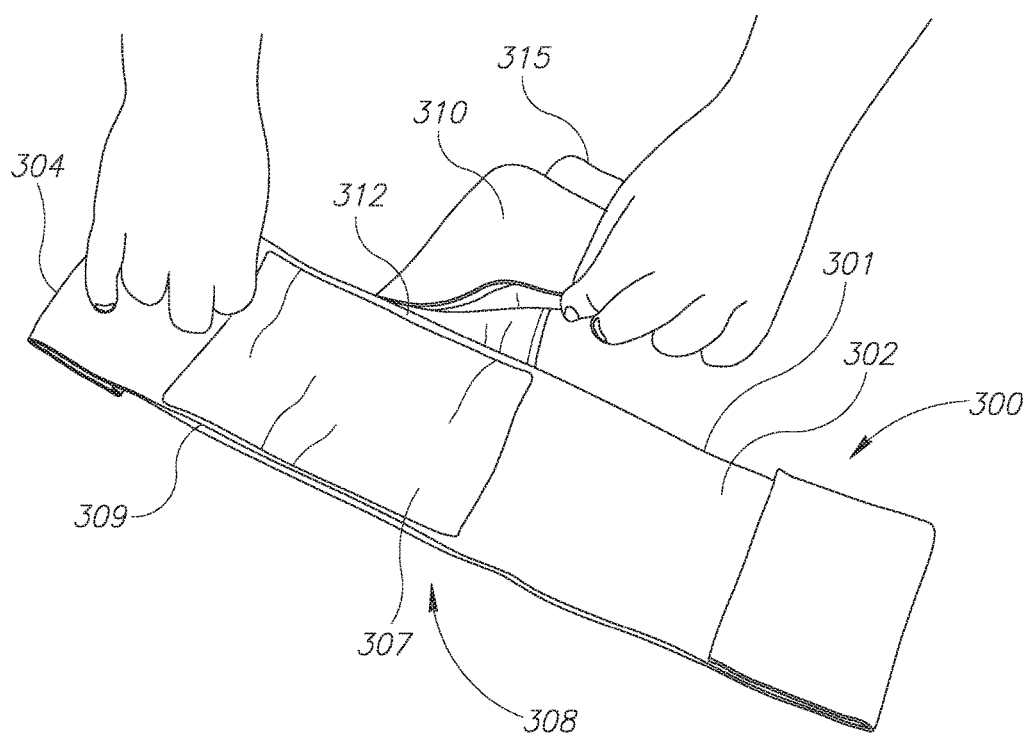

Reference is now made to FIG. 3A, FIG. 3B and FIG. 3C, depicting wound-dressing apparatus (300) according to an embodiment of the present disclosure, in which second portion (310) of foldable pad element (308) is in a folded configuration (FIG. 3A), in an open configuration (FIG. 3B) and during removal of second portion 310 from first portion (309) of foldable pad element (308) (FIG. 3C). Wound-dressing apparatus (300) comprises wrapping element (301), pad element (308), and receptacle (304). Receptacle (304) comprises wound-dressing material (306) which may be extracted through an opening in receptacle (304), as essentially described herein. Optionally, second portion (310) includes a handle, here pull-tab (315), allowing grasping by a user, thereby easing the removal of second portion (310) from first portion (309), as shown in FIG. 3C, First portion (309) of pad element (308) is at least partially attached to first surface (302) of wrapping element (301), such that absorbent layer (307) faces away from first surface (302) and towards the subject to be treated by the disclosed apparatus. Upon pulling of second portion (310) of pad element (308), attachment (312) is torn, enabling removal of second portion (310) from first portion (309).

Figure 4:
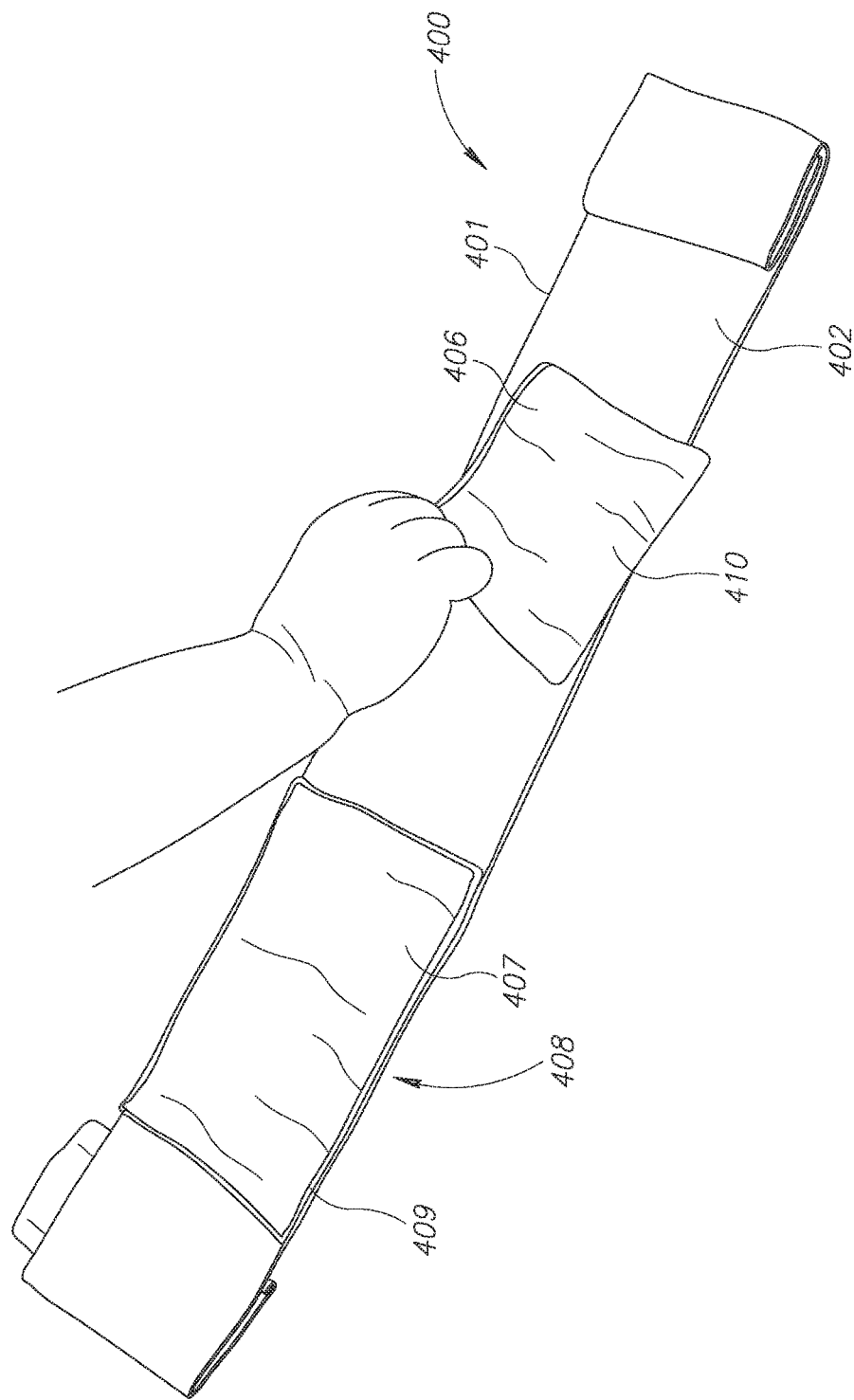
FIG. 4 schematically illustrates a wound-dressing apparatus according to an embodiment of the present disclosure in which the second portion of the pad element is being attached to the wrapping element at a position further from the first portion.

Reference is now made to FIG. 4, depicting wound-dressing apparatus (400) according to an embodiment of the present disclosure, in which the second portion (410) of the foldable pad element (408) has been removed from first portion (409), and is being attached to wrapping element (401). As shown, at least part of first portion (409) is attached to first surface (402) of wrapping element (401). Following removal of second portion (410) from first portion (409), second portion (410) is being attached to another position on first surface (402), such that absorbent layer (406) of second portion (410) is facing away from first surface (402). According to some embodiments, first surface (402) further comprises fixation means for fixing second portion (410) to a desired position on first surface (402). According to exemplary embodiments, the fixation means comprise a hook and loop fastener and/or adhesive tape. Each possibility represents a separate embodiment of the present invention. According to some embodiments, wound-dressing apparatus (400) may be used to treat a complex wound having an entry and an exit wound, such as, but not limited to, a bullet wound, an amputation, a large area wound or a multiple injuries wound. According to some embodiments, when treating a complex wound having an entry and an exit wound, absorbent layer (407) of first portion (409) can be positioned near the entry wound while absorbent layer (406) of second portion (410) can be positioned next to the exit wound. Alternatively, absorbent layer (406) of second portion (410) can be positioned near the entry wound while absorbent layer (407) of first portion (409) can be positioned next to the exit wound. Wrapping element (401) may then be wrapped around the first portion (409) and second portion (410), thus enabling treating both entry and exit wounds using the disclosed apparatus. Alternatively, removed second portion (410) may be used for packing a single wound by placing absorbent layer (406) of second portion (410) facing towards the wound and subsequently wrapping apparatus 400 over second portion (410), such that first portion (409) is aligned with second portion (410).

Reference is now made to FIG. 5, depicting wound-dressing apparatus (500) according to an embodiment of the present disclosure, comprising wrapping element (501) and folded pad element (508) attached to first surface (502) of wrapping element (501). Compartment (504) is situated at one end of wrapping element (501), and includes a wound-dressing material (506) configured to be extracted through an opening in compartment (504). According to some embodiments, wound-dressing material (506) may be used for cleaning the wound and/or packing the wound. Each possibility represents a separate embodiment of the present invention. According to some embodiments, wound-dressing material (506) may be folded such that it is extractable from compartment (504) by pulling dressing material (506). According to some embodiments, dressing material (506) is configured to be extracted from compartment (504) following a single pull. According to some embodiments, wound-dressing material (506) is folded within compartment (504) prior to extraction in a fold such as, but not limited to, a z-fold.

Figure 6B:
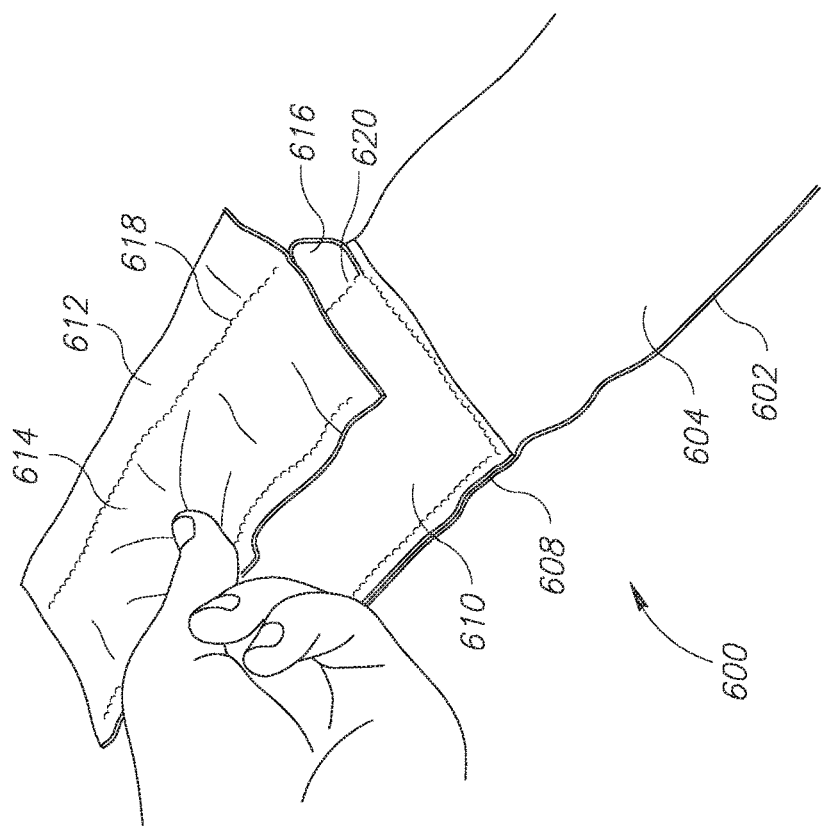
FIGS. 6A-6C schematically illustrate a wound-dressing apparatus according to an embodiment of the present disclosure in which the first portion and second portion of the pad element are attached via at least one absorbent layer.
Figure 6A:
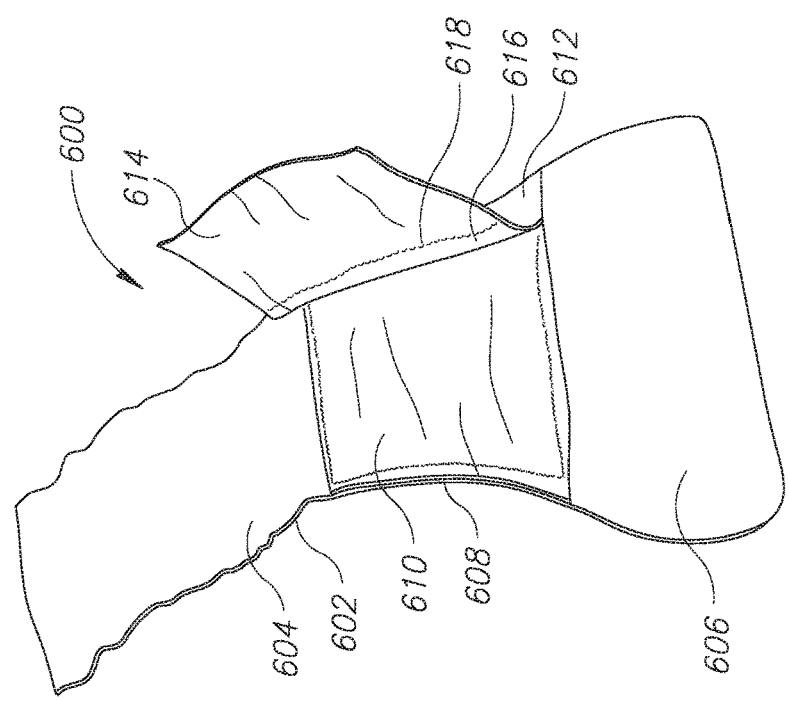

Reference is now being made to FIGS. 6A-6B, depicting a wound-dressing apparatus (600) according to an embodiment of the present disclosure, comprising wrapping element (602) having compartment (606) and further comprising pad element (608) juxtaposed to compartment (606). First portion (610) of pad element (608) is attached to first surface (604) of wrapping element (602). According to some embodiments, first portion (610) is sewed to wrapping element (602).

Figure 6C:
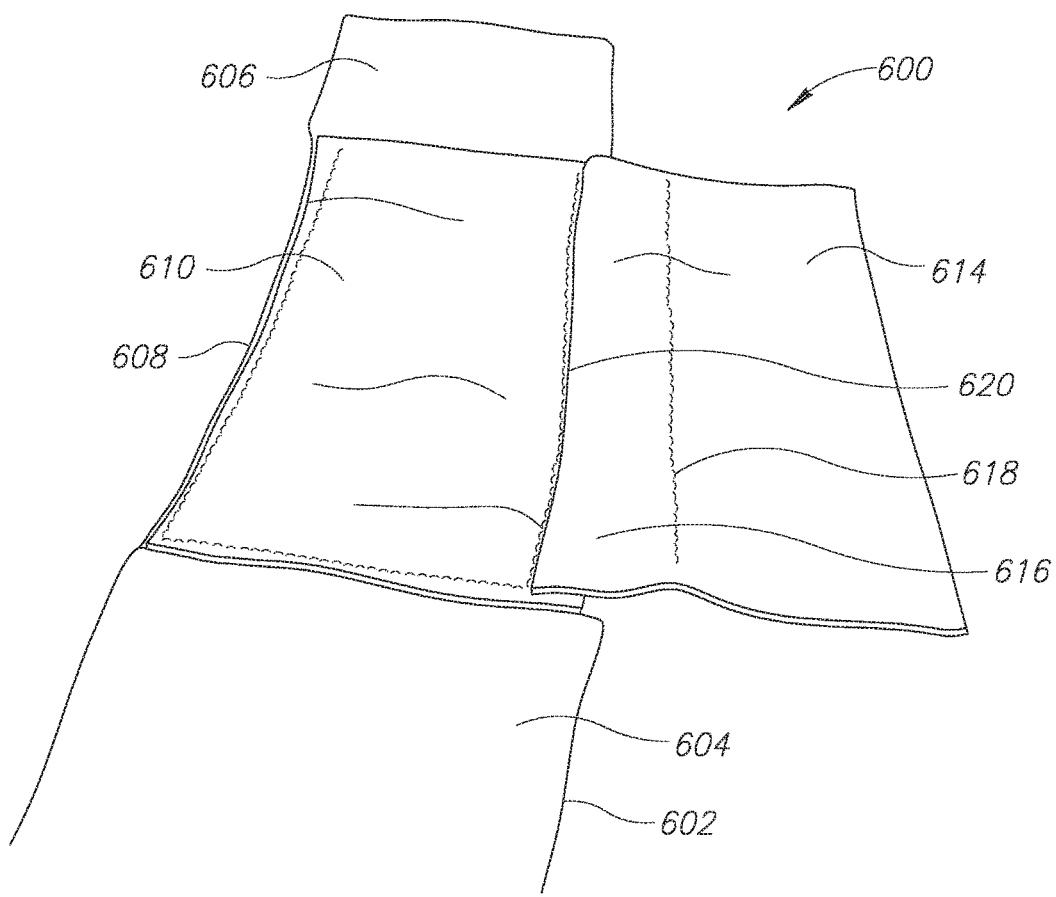

Second portion (614) of pad element (608) is attached to first portion (610). According to some embodiments, second portion (614) of pad element (608) is attached to first portion (610) through at least one layer (616). According to some embodiments, layer (616) may be an absorbent layer. According to some embodiments, layer (616) may be a non-woven fabric. According to some embodiments, layer (616) is attached on one side to first portion (610) along attachment site (620) and on the other side to second portion (614) along attachment site (618). FIGS. 6A and 6C depict second portion (614) at a semi-open and an open position, respectively. FIG. 6B depicts second portion (614) at a semi-closed position.

According to some embodiments, layer (616) covers at least a part of the absorbent layers of the first and/or second portions. Each possibility represents a separate embodiment of the present invention. According to some embodiments, layer (616) is attached to first portion (610) and/or to second portion (614) through sutures. Each possibility represents a separate embodiment of the present invention. According to some embodiments, layer (616) is attached to second portion (614) such that at least part (612) of second portion (614) is located under layer (616) and/or partially overlaps with first portion (610) when second portion (614) is in the open position. Each possibility represents a separate embodiment of the present invention. According to some embodiments, part (612) is defined by attachment site (618) and one end of second portion (614). According to some embodiments, attachment site (620) is located inwardly (for example approximately 0.5, 1, 1.5, 2, 3 cm—each possibility is a separate embodiment) from a first edge of first portion (610). According to some embodiments, attachment site (618) is located inwardly (for example approximately 0.5, 1, 1.5, 2, 3 cm—each possibility is a separate embodiment) from a first edge of second portion (614). As a result, when pad element (608) is unfolded (spread) (see FIG. 6C) a partial overlap exists between first portion (610) and second portion (614) along the length of layer (616). This structure creates a continuous absorbent layer devoid of a gap between first portion (610) and second portion (614). When pad element (608) is folded first portion (610) and second portion (614) lay essentially accurately on top of each other creating an essentially even double layer having an essentially even absorption capability.

According to some embodiments, layer (616) is configured to be torn. According to some embodiments, the area of layer (616) which lies between attachment site (618) and attachment site (620) is configured to be torn. According to some embodiments, layer (616) is configured to be torn upon pulling of second portion (614) such that second portion (614) may be removed from first portion (610). According to some embodiments, attaching second portion (614) to first portion (610) via a single layer enables quick removal of second portion (614).

Without wishing to be bound by any mechanism, the area of layer (616) which lies between attachment site (618) and attachment site (620) enables movement of second portion (614) relative to first portion (610) such that it enables one to place second portion (614) over all or part of first portion (610), as required. According to some embodiments, both faces of the second portion comprise absorbent layers, such that the second portion may provide drainage of the wound when folded over the first portion or part thereof.

According to some embodiments, the present disclosure provides a wound-dressing apparatus, the apparatus comprising an elongated wrapping element and a foldable pad element;
  wherein said elongated wrapping element:
    has a first end and a second end; wherein one of said first or second ends comprises a compartment having at least one opening; wherein said compartment contains wound-dressing material; and wherein said wound dressing material is configured to be extracted from said compartment upon pulling;

and wherein said pad element:

comprises a first portion attached to a second portion, each portion comprising at least one absorbent layer; wherein said first portion is attached to a first surface of said wrapping element such that said at least one absorbent layer faces away from said first surface;

wherein said second portion is configured to have an open position and a closed position, such that when said second portion is in the open position, said at least one absorbent layer faces away from the first surface of said wrapping element;

and wherein said second portion is configured to be removed from said first portion.

According to some embodiments, the present disclosure provides a method of treating a wound, the method comprising placing at least the first portion of the foldable pad element of the disclosed apparatus over a wound of a subject in need thereof and securing said at least first portion using the elongated wrapping element. According to some embodiments, the method further comprising placing the second portion of the foldable pad element over another wound and securing both first and second portions of the foldable pad element using the wrapping element. According to some embodiments, securing using the wrapping element is performed by wrapping the element around a limb/trunk afflicted with the wound. Each possibility represents a separate embodiment of the present invention. According to some embodiments, the disclosed method further comprises packing the wound using the wound-dressing material and/or the second portion of the foldable pad element. Each possibility represents a separate embodiment of the present invention.

The terms "comprises", "comprising", "includes", "including", "having" and their conjugates, as used herein, mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure. In the description and claims of the application, each of the words "comprise" "include" and "have", and forms thereof, are not necessarily limited to members in a list with which the words may be associated.

As used herein, the singular form "a", "an" and "the" include plural references unless the context clearly dictates otherwise. For example, the term "a compound" or "at least one compound" may include a plurality of compounds, including mixtures thereof.

As used herein the term "about" refers to plus/minus 10% of the value stated. As used herein, the term "plurality" refers to at least two.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

What is claimed is:

1. A wound-dressing apparatus, the apparatus comprising:
an elongated wrapping element; and
a foldable pad element;
wherein said pad element comprises a first portion attached to a second portion, each portion comprising at least one absorbent layer;
wherein at least part of said first portion is attached to a first surface of said wrapping element such that said at least one absorbent layer faces away from said first surface;
wherein said second portion is configured to have an open position and a closed position, such that when said second portion is in the open position, said at least one absorbent layer faces away from the first surface of said wrapping element;
wherein said second portion is configured to be removed from said first portion, and
wherein said second portion extends beyond said first portion and said first surface of the wrapping element when in said open position.

2. The wound-dressing apparatus of claim 1, wherein said elongated wrapping element has a first and second end; wherein one of said first or second ends of said elongated wrapping element comprises a compartment having at least one opening; wherein said compartment contains wound-dressing material; and wherein said wound dressing material is configured to be extracted from said compartment upon pulling.

3. The wound-dressing apparatus of claim 2, wherein said first portion of the pad element is juxtaposed with said compartment in the wrapping element.

4. The wound-dressing apparatus of claim 2, wherein said wrapping element is elastic and wherein said wound-dressing material is selected from the group consisting of: gauze, a bandage and a combination thereof.

5. The wound-dressing apparatus of claim 2, wherein said wound-dressing material is configured to be extracted from said compartment following a single pulling movement.

6. The wound-dressing apparatus of claim 1, wherein at least part of said first portion is integrally formed with said first surface of the wrapping element.

7. The wound-dressing apparatus of claim 1, wherein said second portion is configured to be at least partly folded over said first portion when in said closed position.

8. The wound-dressing apparatus of claim 7, wherein said at least one absorbent layer of said second portion is configured to face said at least one absorbent layer of said first portion when in said closed position.

9. The wound-dressing apparatus of claim 1, wherein said second portion is reversibly attached to or folded over said first portion.

10. The wound-dressing apparatus of claim 1, wherein said second portion is attached to said first portion via at least one layer; and wherein said at least one layer is attached to said first and second portions on opposing ends.

11. The wound-dressing apparatus of claim 10, wherein said at least one layer is an absorbent layer.

12. The wound-dressing apparatus of claim 10, wherein at least part of said second portion is configured to be positioned below said at least one layer when in the open position.

13. The wound-dressing apparatus of claim 1, wherein said second portion is configured to be removed from said first portion upon pulling of said second portion.

14. The wound-dressing apparatus of claim 13, wherein said second portion is configured to be removed from said first portion following a single pulling movement of said second portion.

15. The wound-dressing apparatus of claim 1, wherein said second portion is configured to be attached to said first surface of said wrapping element following removal from said first portion.

16. The wound-dressing apparatus of claim 15, wherein said first surface of said wrapping element comprises fixation means configured to attach said second portion to said first surface.

17. The wound-dressing apparatus of claim 16, wherein said fixation means are selected from the group consisting of: adhesive strips, hook and loop fasteners and a combination thereof.

18. The wound-dressing apparatus of claim 1, wherein said pad element further comprises a third portion attached to said first portion; wherein said third portion is configured to have an open position and a closed position, such that when said third portion is in the open position, at least one absorbent layer of said third portion faces away from the first surface of said wrapping element; and wherein said third portion is configured to be removed from said first portion.

19. The wound-dressing apparatus of claim 1 for use in treating a complex wound; wherein said apparatus is for use in treating a complex wound having at least an entry wound and an exit wound.

* * * * *